United States Patent [19]

Spiegel

[11] 4,289,780
[45] Sep. 15, 1981

[54] METHODS OF TREATING SLEEP DISTURBANCE

[75] Inventor: Rene Spiegel, Binningen, Switzerland

[73] Assignee: Sandoz Ltd., Basel, Switzerland

[21] Appl. No.: 138,090

[22] Filed: Apr. 7, 1980

[30] Foreign Application Priority Data

Apr. 12, 1979 [GB] United Kingdom ............... 12923/79

[51] Int. Cl.³ .......................................... A61K 31/447
[52] U.S. Cl. .................................................... 424/267
[58] Field of Search ........................................ 424/267

[56] References Cited

PUBLICATIONS

Chem. Abst. 82-156102p, (1975).

Primary Examiner—Stanley J. Friedman
Attorney, Agent, or Firm—Gerald D. Sharkin; Robert S. Honor

[57] ABSTRACT

Method of treating sleep disturbance which comprises administering a compound of formula

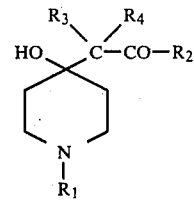

wherein $R_1$ is phenethyl or butyrophenone optionally mono-substituted in the phenyl ring by fluorine, chlorine, bromine or lower alkyl or alkoxy, $R_2$ is $OR_5$ wherein $R_5$ is lower alkyl or alkenyl or phenyl optionally mono-substituted by fluorine, chlorine, bromine, or alkoxy; or $N(R_6)R_7$ wherein $R_6$ and $R_7$ are each hydrogen, lower alkyl or cycloalkylalkyl, cycloalkyl, phenyl optionally mono-substituted by fluorine, chlorine, bromine, lower alkyl or lower alkoxy or lower phenylalkyl optionally mono-substituted in the phenyl ring by fluorine, chlorine, bromine or lower alkyl or alkoxy or $R_6$ and $R_7$ together with the nitrogen atom to which they are bound form a saturated heterocycle of 5 to 6 ring members, and either $R_3$ is lower alkyl or cycloalkylalkyl, cycloalkyl or phenyl optionally mono-substituted by fluorine, chlorine, bromine or lower alkyl or alkoxy or, when $R_1$ is optionally mono-substituted phenethyl, also lower alkenyl and $R_4$ is hydrogen or $R_3$ and $R_4$ together with the carbon atom to which they are bound form a $C_{4-6}$-cycloalkyl ring.

7 Claims, No Drawings

METHODS OF TREATING SLEEP DISTURBANCE

This invention relates to a new use for the compounds of formula I,

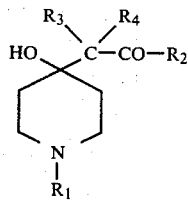

wherein
- $R_1$ is phenethyl, phenethyl monosubstituted in the phenyl ring by fluorine, chlorine, bromine, lower alkyl or lower alkoxy, butyrophenone or butyrophenone monosubstituted in the phenyl ring by fluorine, chlorine, bromine, lower alkyl or lower alkoxy,
- $R_2$ is an $OR_5$ group,
  wherein $R_5$ is lower alkyl, lower alkenyl, phenyl or phenyl monosubstituted by fluorine, chlorine, bromine, lower alkyl or lower alkoxy,
  or an

group,
wherein independently each of
- $R_6$ and $R_7$ is hydrogen, lower alkyl or cycloalkylalkyl, cycloalkyl, phenyl, phenyl monosubstituted by fluorine, chlorine, bromine, lower alkyl or lower alkoxy, lower phenylalkyl or lower phenylalkyl monosubstituted in the phenyl ring by fluorine, chlorine, bromine, lower alkyl or lower alkoxy, or wherein
- $R_6$ and $R_7$ together with the nitrogen atom to which they are bound, form a saturated heterocycle of 5 to 6 ring members, which may optionally contain as second hetero atom oxygen, sulphur or nitrogen substituted by lower alkyl,
- $R_3$ is lower alkyl or cycloalkylalkyl, cycloalkyl, phenyl or phenyl monosubstituted by fluorine, chlorine, bromine, lower alkyl or lower alkoxy, or when $R_1$ is phenethyl or phenethyl monosubstituted in the phenyl ring by fluorine, chlorine, bromine, lower alkyl or lower alkoxy, alternatively lower alkenyl, and
- $R_4$ is hydrogen or lower alkyl, or
- $R_3$ and $R_4$ together with the carbon atom to which they are bound form a cycloalkyl ring of 4 to 6 carbon atoms.

These compounds are known and are described in for example DOS No. 24 29,373 and G.B. Patent Specification No. 1,475,151, the contents of which are hereby incorporated by reference.

The compounds have been proposed for use as analgesic, anti-migraine and anti-depressant agents as indicated in vitro and/or animal tests. The compounds are also well tolerated, exhibiting a zero toxic effect level of the order of 20 mg/kg/day in the dog over a 13 week period.

In accordance with the present invention it has now surprisingly been found that the compounds of formula I are also useful as hypnotic agents for treating sleep disturbance e.g. as encountered in elderly subjects, for example for promoting the onset of sleep and for the improvement of sleep. Thus in clinical trials as hereinafter described it has unexpectedly been found that administration of compounds of formula I leads e.g. to an increase in deep-sleep and to a reduction of sleep disturbance, such as waking and restless phases, as well as a decrease in body movements during sleep.

Accordingly in a first aspect the present invention provides a method of treating sleep disturbance in a subject in need of such treatment, which method comprises administering an effective amount of a compound of formula I as defined above.

Preferred compounds of the formula I for use in accordance with the method of the invention are those of the formula Ia,

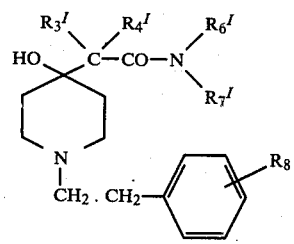

wherein
- $R_3{}^I$ is $C_{1-4}$-alkyl,
- $R_4{}^I$ and $R_6{}^I$ are independently hydrogen or $C_{1-4}$-alkyl,
- $R_7{}^I$ is $C_{1-4}$-alkyl, $C_{4-6}$-cycloalkyl or $C_{4-6}$-cycloalkyl-$C_{1-4}$-alkyl, and
- $R_8$ is hydrogen, bromine, chlorine, fluorine or $C_{1-4}$-alkyl.

Preferred compounds are 1-o-chlorophenylethyl-N-cyclohexyl-4-hydroxy-α,α,N-trimethyl-4-piperidine acetamide (hereinafter referred to as compound A), and 2-(1-o-chlorophenethyl-4-hydroxy-4-piperidyl)-N-cyclohexyl-N-methyl propionic acid amide (hereinafter referred to as compound B).

The hypnotic activity of the compounds may be shown as follows:

In one trial 8 healthy male volunteers aged from 20 to 40 were involved. Each volunteer was administered a placebo capsule or a dose of 25, 50 or 100 mg of compound A) at random at 10 p.m. on each of 5 consecutive nights, the placebo being administered on 2 of the nights. No information was provided as to whether the placebo or active ingredient was being administered.

After administration the patient was allowed to sleep for 8 hours. The EEG (electroencephalogram), EOG (electrooculogram) and EMG (electromyogram) were recorded according to conventional techniques (Rechtschafen and Kales, A Manual of Standardised Terminology, Techniques, and Scoring System for Sleep Stages of Human Subjects, U.S. Department of Health Education and Welfare, 1968).

A dose dependent prolongation of slow wave sleep (SWS) (deep sleep), especially stage 4 sleep was observed, together with a dose dependent reduction of NREM-changes and other sleep disturbances.

The volunteers reported that they experienced an improvement of sleep and a reduction in number of subjectively experienced sleep interruptions, which was also dose dependent.

A second trial was conducted on similar lines employing 9 male volunteers. In this trial each volunteer was administered a placebo capsule or a dose of 100 or 200 mg of compound B) at random, the placebo being administered on three nights.

In this instance increases of slow-wave sleep at the expense of stage 2 sleep of the order of 50% and 65% were observed on administration of 100 mg and 200 mg units of compound B) respectively. There was also a reduction of waking and restless phases during sleep. After administration of 200 mg doses, a reduction of the number of body movements was observed during the third part of the night.

Again the volunteers reported a subjectively deeper and less frequently interrupted sleep after administration of compound B).

The dosage employed in treating sleep disturbance in accordance with the invention will of course vary according to e.g. the specific compound employed, the mode of administration, the condition to be treated and the therapy desired. In general however for larger mammals the compound will be administered at a dosage of from about 20 to about 300, preferably to about 200 mg, once a day prior to sleep. A preferred dosage range is from about 50 to about 250 mg, and the most preferred range is from 100 to 200 mg.

In accordance with the invention the compound of the formula I may of course be administered in free base form or in pharmaceutically acceptable acid addition salt form. Such salt forms exhibit the same order of activity as the free base forms and are readily prepared in conventional manner. Representative acid addition salt forms include organic acid salt forms such as the hydrogen maleate, fumarate, tartarate and mesylate and mineral acid salt forms such as the hydrochloride, hydrobromide and sulphate. For use in accordance with the invention the compounds of the formula I are suitably put up as pharmaceutical compositions, e.g. in unit dosage forms containing for example 100 or 200 mg of the compound of formula I per unit dosage.

Such compositions may be prepared by conventional techniques to be in conventional forms, for example, capsules, tablets, suppositories, dispersible powders, syrups, elixirs, suspensions or solutions, for enteral or parenteral administration. Suitable pharmaceutical diluents or carriers include, for example, water, alcohols, natural or hardened oils and waxes, calcium and sodium carbonates, calcium phosphate, kaolin, talc and lactose as well as suitable preserving agents such as methyl cellulose, tragacanth and sodium alginate, wetting agents such as lecithin, polyoxyethylene stearate and polyoxyethylene sorbitan mono-oleate, granulating and disintegrating agents such as starch and alginic acid, binding agents such as starch, gelatin and acacia, and lubricating agents such as magnesium stearate, stearic acid and talc, in order to provide an elegant and palatable pharmaceutical preparation. Compositions in tablet form may be coated by conventional techniques to delay disintegration of the tablet and absorption of the active ingredient in the gastro-intestinal tract and thereby provide sustained action over a long period.

The preferred compositions from the stand-point of ease of administration are solid compositions, particularly solid-filled gelatin capsules and tablets. Examples of suitable compositions are given below.

In accordance with the foregoing the present invention also provides a pack containing a pharmaceutical composition comprising a compound of formula I as herein defined together with instructions for the administration of said composition for the treatment of sleep disturbance. Preferably the composition is in unit dosage form suitable e.g. for oral administration. The instructions may for example be printed on the pack.

EXAMPLE 1

| (a) Capsules | |
|---|---|
| Composition: | |
| 2-(1-o-chlorophenethyl-4-hydroxy-4-piperidyl)-N-cyclohexyl-N-methyl propionic acid amide hydrogen maleate | 32.125 mg (= 25 mg base) |
| Excipient mixture: | 310.875 mg |
| [Corn Starch 58.5% Lactose (200 mesh) 40% Colloidal silica 0.5% Magnesium stearate 1%] | |
| yields one capsule of | 343 mg |

The capsule is produced according to conventional methods.

| (b) Capsules | |
|---|---|
| Composition: | |
| 2-(1-o-chlorophenethyl-4-hydroxy-4-piperidyl)-N-cyclohexyl-N-methyl propionic acid amide hydrogen maleate | 128.5 mg (= 100 mg base) |
| Excipient mixture: | 181.5 mg |
| [Lactose (200 mesh) 58.5% Corn starch 40.0% Colloidal silica 0.5% Magnesium stearate 1.0%] | |
| yields one capsule of | 310.0 mg |

The capsule is produced according to conventional methods.

EXAMPLE 2

| (a) Capsules | | |
|---|---|---|
| Composition: 1-o-chlorophenethyl-N-cyclohexyl-4-hydroxy-$\alpha,\alpha$-N-trimethyl-4-piperidine acetamide mesylate | 25 | mg |
| Lactose (200 mesh) | 184.6 | mg |
| Corn Starch | 137.6 | mg |
| Colloidal Silica | 1.05 | mg |
| Magnesium Stearate | 1.75 | mg |
| yields one capsule of | 350 | mg |

The capsule is produced according to conventional methods.

| (b) Capsules | | |
|---|---|---|
| Composition: 1-o-chlorophenethyl-N-cyclohexyl-4-hydroxy-$\alpha,\alpha$-N-trimethyl-4-piperidine acetamide mesylate | 100 | mg |
| Lactose (200 mesh) | 105 | mg |
| Anhydrous lactose | 72.025 | mg |
| Corn starch | 70.0 | mg |
| Colloidal silica | 1.225 | mg |
| Magnesium stearate | 1.75 | mg |
| yields one capsule of | 350.00 | mg |

I claim:

1. A method of treating sleep disturbance in a subject in need of such treatment, which method comprises administering to said subject an amount sufficient to treat sleep disturbance of a compound of formula Ia

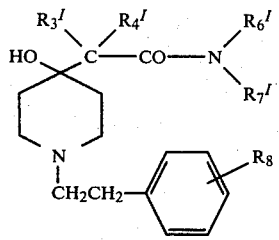

wherein
$R_3{}^I$ is $C_{1-4}$-alkyl,
$R_4{}^I$ and $R_6{}^I$ are independently hydrogen or $C_{1-4}$-alkyl,
$R_7{}^I$ is $C_{1-4}$-alkyl, $C_{4-6}$-cycloalkyl or $C_{4-6}$-cycloalkyl-$C_{1-4}$-alkyl, and
$R_8$ is hydrogen, bromine, chlorine, fluorine or $C_{1-4}$-alkyl,
or a pharmaceutically acceptable acid addition salt thereof.

2. A method according to claim 1, wherein the compound of formula Ia is 1-o-chlorophenethyl-N-cyclohexyl-4-hydroxy-α,α,N-trimethyl-4-piperidine acetamide.

3. A method according to claim 1, wherein the compound of formula Ia is 2-(1-o-chlorophenethyl-4-hydroxy-4-piperidyl)-N-cyclohexyl-N-methyl propionic acid amide.

4. A method according to claim 1 wherein the compound is administered at a dose of from about 50 to about 250 mg.

5. A method according to claim 4, wherein the compound is administered at a dose of from about 100 to about 200 mg.

6. The method of claim 1 wherein said subject is a larger mammal.

7. A method according to claim 1, wherein the compound administered is of the formula

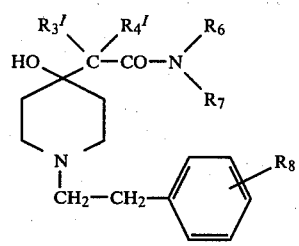

wherein
$R_3{}^I$, $R_4{}^I$ and $R_8$ are as defined in claim 2,
$R_6$ is $C_{1-4}$ alkyl, and
$R_7$ is $C_{4-6}$ cycloalkyl,
or a pharmaceutically acceptable acid addition salt thereof.

* * * * *